US006232118B1

(12) United States Patent
Fürst et al.

(10) Patent No.: US 6,232,118 B1
(45) Date of Patent: May 15, 2001

(54) PROTEIN INDUCED BY DEPRENYL

(75) Inventors: Peter Fürst, Rheinfelden; Peter Waldmeier, Ettingen, both of (CH); William George Tatton, Purchase, NY (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/101,519

(22) PCT Filed: Dec. 21, 1996

(86) PCT No.: PCT/EP96/05800

§ 371 Date: Aug. 13, 1998

§ 102(e) Date: Aug. 13, 1998

(87) PCT Pub. No.: WO97/25421

PCT Pub. Date: Jul. 17, 1997

(30) Foreign Application Priority Data

Jan. 12, 1996 (GB) .................................................. 9600660

(51) Int. Cl.⁷ ............................. C12N 15/12; C07H 21/04
(52) U.S. Cl. .................... 435/325; 435/320.1; 435/252.3; 536/23.5; 530/350
(58) Field of Search ................... 435/471, 320.1, 435/252.3, 325; 536/23.1, 23.4, 23.5, 24.1, 24.2, 24.5, 24.31, 24.32, 24.33; 530/350

(56) References Cited

FOREIGN PATENT DOCUMENTS

| 239400 | 9/1987 | (EP) . |
| 90/07861 | 7/1990 | (WO) . |
| 95/00642 | 1/1995 | (WO) . |

OTHER PUBLICATIONS

Matthias, P. et al., Nucleic Acid Research, vol. 17, p. 6418 (1989).
Min et al., Mo. Brain Res., vol. 27, pp. 281–289 (1994).
Tatton et al., Movement Disorders, vol. 9, Suppl. 1, p. 4 (1994).
Tatton et al., J. Neurochemistry, vol. 63, pp. 1572–1575 (1994).
Wesselingh et al., Database EMBL Sequence RN10579, "Cloning and expression of rat bc1–x in cultured neurons", Accession number U10579 (1995).
Benjamin, Genes IV, p. 810, Definintition Gene, Oxford Univ. Press, 1990.*
Webster's New World Dictionary, Third College Ed., p. 634, Defn. Heterologous, 1988.*
Lazar et al, Mol. & Cell Biol., 8(3):1247–52, 1988.*
Burgess et al., J. of Cell Biol., vol. 111, p. 2129–2138, 1990.*
Salgaller et al, Cancer Immunol. Immunother., 39:105–116, 1994.*
GenEmbl Accession U10579, Hardwick, Jun. 28, 1994.*
Fang et al, J. Immunol., 153(10):4388–98, 1994.*
Sambrook et al, Molecular Cloning, Cold Spring Harbor Labs., 16.2–16.16, 1989.*

* cited by examiner

Primary Examiner—Lorraine Spector
(74) Attorney, Agent, or Firm—Hesna J. Pfeiffer

(57) ABSTRACT

We have found that Deprenyl® induces a novel polypeptide in neural cells. This polypeptide has the structure given in SEQ ID No. 1 and is referred to herein as DIP 1 (Deprenyl® Induced Protein 1).

4 Claims, No Drawings

SEQUENCE LISTING

<160> NUMBER OF SEQ ID NOS: 1

<210> SEQ ID NO: 1
<211> LENGTH: 225
<212> TYPE: PRT
<213> ORGANISM: rat-derived

<400> SEQUENCE: 1

Met Ser Gln Ser Ala Asn Arg Glu Leu Val Val Asp Ser Leu Ser Tyr
 1               5                   10                  15

-continued

```
Lys Leu Ser Gln Lys Gly Tyr Ser Trp Ser Gln Phe Ser Asx Val Glu
            20                  25                  30
Glu Asn Arg Thr Arg Glu Thr Pro Ser Ala Ile Asn Gly Asn Pro Ser
            35                  40                  45
Trp His Leu Ala Asx Ser Pro Glu Val Asn Gly Ala Thr Gly His Ser
            50                  55                  60
Ser Ser Leu Asp Ala Arg Glu Val Ile Pro Met Ala Ala Val Lys Gln
 65                  70                  75                  80
Ala Leu Arg Glu Ala Gly Asp Glu Phe Glu Leu Arg Tyr Arg Arg Ala
            85                  90                  95
Phe Ser Asp Leu Thr Ser Gln Leu His Ile Thr Pro Gly Thr Ala Tyr
            100                 105                 110
Gln Ser Phe Glu Gln Val Val Asn Glu Leu Phe Arg Asp Gly Val Asn
            115                 120                 125
Trp Gly Arg Ile Val Ala Phe Phe Ser Phe Gly Gly Ala Leu Cys Val
            130                 135                 140
Glu Ser Val Asp Lys Glu Met Gln Val Leu Val Ser Arg Ile Ala Ser
145                 150                 155                 160
Trp Met Ala Thr Tyr Leu Asn Asp His Leu Glu Pro Trp Ile Gln Glu
            165                 170                 175
Asn Gly Gly Trp Asp Thr Phe Val Asp Leu Tyr Gly Asn Asn Ala Ala
            180                 185                 190
Ala Glu Ser Arg Lys Gly Gln Glu Arg Phe Asn Arg Trp Phe Leu Thr
            195                 200                 205
Gly Met Thr Val Ala Gly Val Val Leu Leu Gly Ser Leu Phe Ser Arg
    210                 215                 220
Lys
225
```

PROTEIN INDUCED BY DEPRENYL

The present invention relates to a novel polypeptide which is induced by a neuroactive drug, to sequences encoding this polypeptide and to uses thereof.

Damaged cells, cells receiving inadequate trophic support or conflicting signals, or deprived of their targets eliminate themselves by means of programmed cell death or apoptosis, leading to their clean demise, leaving no traces. Evidence is accumulating that neuronal cell death in many neurodegenerative diseases including Alzheimer's, Parkinson's, Huntington's disease, amyotrophic lateral sclerosis, cerebellar degeneration, and oligodendrocyte death in multiple sclerosis, is associated with apoptosis. Rescuing cells from apoptosis may halt progression of neurodegenerative diseases, provided the rescued cells remain functional.

(−)—Deprenyl® (Formula 1; referred to herein as Deprenyl®) delays the progression of Parkinson's disease and rescues neurones from presumably apoptotic cell death in a number of in vivo paradigms (death of facial motoneurones after axotomy; destruction of dopaminergic cells in substantia nigra by MPTP or MPP+; death of $CA_1$ hippocampal neurones after unilateral carotid occlusion followed by a brief period of hypoxia; death of hippocampal pyramidal cells after systemic kainate administration; death of retinal ganglion cells after optic nerve crush) as well as in vitro in trophic factor deprived PC12 cells and oligodendrocytes by an as yet unidentified mechanism.

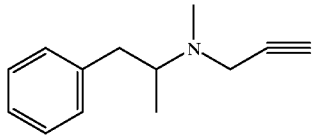

(Formula 1)

Deprenyl® is metabolised via (−)—desmethyideprenyl to (−)—methamphetamine and (−)—amphetamine, both of which potently antagonise Deprenyl®'s rescuing effects in vivo and in vitro. Therefore, compounds with equal or better neurorescuing properties than Deprenyl®, but unable to generate antagonistic metabolites, may show a higher therapeutic efficacy in the treatment of neurodegenerative diseases.

We have now found that Deprenyl® induces a novel polypeptide in neural cells. This polypeptide has the structure given in SEQ ID No. 1 and is referred to herein as DIP 1 (Deprenyl® Induced Protein 1).

Accordingly, we provide DIP 1, which preferably has the structure shown in SEQ ID No. 1. The recited sequence is that of rat DIP 1, but the invention relates to DIP 1 derived from all sources, including human DIP 1. Species homologues of rat DIP 1 may be obtained using the recited sequence according to standard methodology, as set out below.

The invention also includes functional derivatives of the polypeptide of SEQ ID No. 1.

"Functional derivative" means that the derivative in question at least one functional determinant of DIP 1. Such functions include the susceptibility to induction by Deprenyl®, and/or at least one in vivo function of DIP 1. For example, derivatives of DIP 1 according to the invention may be able to inhibit or postpone apoptotic neural degeneration. Thus, DIP 1 as provided by the present invention includes splice variants encoded by mRNA generated by alternative splicing of a primary transcript, amino acid mutants, posttranslational modifications, such as glycosylation and phosphorylation variants, and other covalent derivatives of DIP 1 which retain the physiological and/or physical properties of DIP 1. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope, or other detectable labels, tags, toxins and genes such as oncogenes and tumour suppressor genes. Further included are naturally occurring variants of DIP 1 found within a particular species, preferably a mammal. Such a variant may be encoded by a related gene of the same gene family, by an allelic variant of a particular gene, or represent an alternative splicing variant of the DIP 1 gene.

Derivatives which retain common functional determinants can be fragments of DIP 1. Fragments of DIP 1 comprise individual domains thereof, as well as smaller polypeptides derived from the domains. Preferably, smaller polypeptides derived from DIP 1 according to the invention define a single functional activity which is characteristic of DIP 1. Fragments may in theory be almost any size, as long as they retain one characteristic of DIP 1. Preferably, fragments will be between 5 and 200 amino acids in length. Longer fragments are regarded as truncations of the full-length DIP 1 and generally encompassed by the term "DIP 1".

Derivatives of DIP 1 also comprise mutants thereof, which may contain amino acid deletions, additions or substitutions, subject to the requirement to maintain at least one feature characteristic of DIP 1. Thus, conservative amino acid substitutions may be made substantially without altering the nature of DIP 1, as may truncations from the 5' or 3' ends. Deletions and substitutions may moreover be made to the fragments of DIP 1 comprised by the invention. DIP 1 mutants may be produced from a DNA encoding DIP 1 which has been subjected to in vitro mutagenesis resulting e.g. in an addition, exchange and/or deletion of one or more amino acids. For example, substitutional, deletional or insertional variants of DIP 1 can be prepared by recombinant methods and screened for functional similarity to the native forms of DIP 1.

The fragments, mutants and other derivatives of DIP 1 preferably retain substantial homology with DIP 1. As used herein, "homology" means that the two entities share sufficient characteristics for the skilled person to determine that they are similar in origin and function. Preferably, homology is used to refer to sequence identity. Thus, the derivatives of DIP 1 preferably retain substantial sequence identity with the sequence of SEQ ID No. 1.

"Substantial homology", where homology indicates sequence identity, means more than 50% sequence identity, preferably more than 75% sequence identity and most preferably a sequence identity of 90% or more.

Preferably, the protein or derivative thereof of the invention is provided in isolated form. "Isolated" means that the protein or derivative has been identified and is free of one OF more components of its natural environment. Isolated DIP 1 includes DIP 1 in a recombinant cell culture. DIP 1 present in an organism expressing a recombinant DIP 1 gene, whether the DIP 1 protein is "isolated" or otherwise, is included within the scope of the present invention.

DIP 1 is believed to be a member of the bcl family of proteins, and is closely homologous to bcl xL. There are, however, characteristic differences between the two proteins which will be apparent by comparing the sequence given herein with the published sequence of rat bcl xL.

The polypeptide according to the invention is closely associated with neurodegenerative disorders and particularly apoptosis in neural cells. Accordingly, the invention provides a composition comprising a polypeptide according to the invention or a modulator thereof for use as a medicament in the treatment or diagnosis of neural diseases.

According to a further aspect of the present invention, there is provided a nucleic acid encoding DIP 1. In addition to being useful for the production of recombinant DIP 1 protein, these nucleic acids are also useful as probes, thus readily enabling those skilled in the art to identify and/or isolate nucleic acid encoding DIP 1. The nucleic acid may be uniabelled or labelled with a detectable moiety. Furthermore, nucleic acid according to the invention is useful e.g. in a method determining the presence of DIP 1-specific nucleic acid, said method comprising hybridising the DNA (or RNA) encoding (or complementary to) DIP 1 to test sample nucleic acid and determining the presence of DIP 1. In another aspect, the invention provides nucleic acid sequence that is complementary to, or hybridises under stringent conditions to, a nucleic acid sequence encoding DIP 1.

The invention also provides a method for amplifying a nucleic acid test sample comprising priming a nucleic acid polymerase (chain) reaction with nucleic acid (DNA or RNA) encoding (or complementary to) DIP 1.

In still another aspect of the invention, the nucleic acid is DNA and further comprises a replicable vector comprising the nucleic acid encoding DIP 1 operably linked to control sequences recognised by a host transformed by the vector. Furthermore the invention provides host cells transformed with such a vector and a method of using a nucleic acid encoding DIP 1 to effect the production of DIP 1, comprising expressing DIP 1 nucleic acid in a culture of the transformed host cells and, if desired, recovering DIP 1 from the host cell culture.

Furthermore, the present invention relates to isolated DIP 1 proteins and derivatives thereof encoded by the above-described nucleic acids.

Isolated DIP 1 nucleic acid includes nucleic acid that is free from at least one contaminant nucleic acid with which it is ordinarily associated in the natural source of DIP 1 nucleic acid or in crude nucleic acid preparations, such as DNA libraries and the like. Isolated nucleic acid thus is present in other than in the form or setting in which it is found in nature. However, isolated DIP 1 encoding nucleic acid includes DIP 1 nucleic acid in ordinarily DIP 1 -expressing cells where the nucleic acid is in a chromosomal location different from that of natural cells or is otherwise flanked by a different DNA sequence than that found in nature.

In accordance with the present invention, there are provided isolated nucleic acids, e.g. DNAs or RNAs, encoding DIP 1, particularly mammalian DIP 1, e.g. rat or human DIP 1, or fragments thereof. In particular, the invention provides a DNA molecule encoding DIP 1, or a fragment thereof. By definition, such a DNA comprises a coding single stranded DNA, a double stranded DNA of said coding DNA and complementary DNA thereto, or this complementary (single stranded) DNA itself.

Preferably, nucleic acids according to the invention are fragments of the DIP 1-encoding sequence, or derivatives thereof as hereinbefore defined in relation to polypeptides. Fragments of the nucleic acid sequence of a few nucleotides in length, preferably 5 to 150 nucleotides in length, are especially useful as probes.

The invention moreover provides functional control elements derived from the DIP 1 gene, such as promoters and enhancers. Such elements are usefully coupled to reporter genes and used to study the modulation of DIP 1 expression by neuroactive drugs at the molecular level. DIP 1-regulated transcription units may be used in cell-based assays, transgenic animals, in methods for gene therapy and other techniques described below.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Given the guidance provided herein, the nucleic acids of the invention are obtainable according to methods well known in the art. For example, a DNA of the invention is obtainable by chemical synthesis, using polymerase chain reaction (PCR) or by screening a genomic library or a suitable cDNA library prepared from a source believed to possess DIP 1 and to express it at a detectable level. Such methods moreover permit the isolation of species homologues of the recited rat DIP 1 by screening nucleic acid sources derived from different species, such as humans.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate the gene encoding DIP 1 is to use PCR technology as described e.g. in section 14 of Sambrook et al., 1989. This method requires the use of oligonucleotide probes that will hybridise to DIP 1 nucleic acid. Strategies for selection of oligonucleotides are described below.

Libraries are screened with probes or analytical tools designed to identify the gene of interest or the protein encoded by it. For cDNA expression libraries suitable means include monoclonal or polyclonal antibodies that recognise and specifically bind to DIP 1; oligonucleotides of about 20 to 80 bases in length that encode known or suspected DIP 1 cDNA from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding DIP 1 may be isolated by screening suitable cDNA or genomic libraries under suitable hybridisation conditions with a probe, i.e. a nucleic acid disclosed herein including oligonucleotides derivable from the sequence set forth in SEQ ID No. 1. Suitable libraries are commercially available or can be prepared e.g. from cell lines, tissue samples, and the like.

As used herein, a probe is e.g. a single-stranded DNA or RNA that has a sequence of nucleotides that includes between 10 and 50, preferably between 15 and 30 and most preferably at least about 20 contiguous bases. The nucleic acid sequences selected as probes should be of sufficient length and sufficiently unambiguous so that false positive results are minimised. The nucleic acids used as probes, being derived from protein sequence, will be degenerate at one or more positions.

Preferred regions from which to construct probes include areas of the DIP 1 sequence which do not share homology with bcl X. Preferably, nucleic acid probes of the invention are labelled with suitable label means for ready detection upon hybridisation. For example, a suitable label means is a radiolabel. The preferred method of labelling a DNA fragment is by incorporating $\alpha^{32}P$ dATP with the Kienow fragment of DNA polymerase in a random priming reaction, as is well known in the art. Oligonucleotides are usually end-labelled with $g^{32P}$-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, e.g. with suitable oligonucleotide, positive clones are identified by detecting a hybridisation signal; the identified clones are characterised by restriction enzyme mapping and/or DNA sequence analysis, and then examined, e.g. by comparison with the sequence set forth herein, to ascertain whether they include DNA encoding a complete DIP 1 (i.e., if they include translation initiation and termination codons). If the selected clones are incomplete, they may be used to rescreen the same or a different library to obtain overlapping clones. If the library is genomic, then the overlapping clones may include exons and introns. If the library is a CDNA library, then the overlapping clones will include an open reading frame. In both instances, complete clones may be identified by comparison with the DNAs and deduced amino acid sequences provided herein.

In order to detect any abnormality of endogenous DIP 1, genetic screening may be carried out using the nucleotide sequences of the invention as hybridisation probes. Also, based on the nucleic acid sequences provided herein antisense-type therapeutic agents may be designed.

It is envisaged that the nucleic acid of the invention can be readily modified by nucleotide substitution, nucleotide deletion, nucleotide insertion or inversion of a nucleofide stretch, and any combination thereof. Such mutants can be used e.g. to produce a DIP 1 mutant that has an amino acid sequence differing from the DIP 1 sequences as found in nature. Mutagenesis may be predetermined (site-specific) or random.

The cDNA or genomic DNA encoding native or mutant DIP 1 can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the $2\mu$ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another organism for expression. For example, a vector is cloned in $E.$ $coli$ and then the same vector is transfected into yeast or mammalian cells even though it is not capable of replicating independently of the host cell chromosome. DNA may also be replicated by insertion into the host genome. However, the recovery of genomic DNA encoding DIP 1 is more complex than that of exogenously replicated vector because restriction enzyme digestion is required to excise DIP 1 DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in $E.$ $coli,$ an $E.$ $coli$ genetic marker and an $E.$ $coli$ origin of replication are advantageously included. These can be obtained from $E.$ $coli$ plasmids, such as pBR322, Bluescript® vector or a pUC plasmid, e.g. pUC18 or pUC 19, which contain both $E.$ $coli$ replication origin and $E.$ $coli$ genetic marker conferring resistance to antibiotics, such as ampicillin.

Suitable selectable markers for mammalian cells are those that enable the identification of cells competent to take up DIP 1 nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes DIP 1. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to DIP 1 nucleic acid. Such a promoter may be inducible or constitutive. The promoters are operably linked to DNA encoding DIP 1 by removing the promoter from the source DNA by restriction enzyme digestion and inserting the isolated promoter sequence into the vector. Both the native DIP 1 promoter sequence and many heterologous promoters may be used to direct amplification and/or expression of DIP 1 DNA.

Promoters suitable for use with prokaryotic hosts include, for example, the blactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding DIP 1, using linkers or adaptors to supply any required restriction sites. Promoters for use in bacterial systems will also generally contain a Shine-Delgarno sequence operably linked to the DNA encoding DIP 1.

Moreover, the DIP 1 gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or a-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide -173 and ending at nucleotide -9 of the PH05 gene.

DIP 1 gene transcription from vectors in mammalian hosts may be controlled by promoters derived from the genomes of viruses such as polyoma virus, adenovirus, fowipox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with DIP 1 sequence, provided such promoters are compatible with the host cell systems.

Transcription of a DNA encoding DIP 1 by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to DIP 1 DNA, but is preferably located at a site 5' from the promoter.

Advantageously, a eukaryotic expression vector encoding DIP 1 may comprise a locus control region (LCR). LCRs are capable of directing high-level integration site independent expression of transgenes integrated into host cell chromatin, which is of importance especially where the DIP 1 gene is to be expressed in the context of a permanently-transfected eukaryotic cell line in which chromosomal integration of the vector has occurred, in vectors designed for gene therapy applications or in transgenic animals.

Suitable eukaryotic host cells for expression of DIP 1 include yeast, fungi, insect, plant, animal, human, or nucleated cells from other multicellular organisms will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding DIP 1.

An expression vector includes any vector capable of expressing DIP 1 nucleic acids that are operatively linked with regulatory sequences, such as promoter regions, that are capable of expression of such DNAS. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding DIP 1 may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding DIP 1 in mammalian cells. Transient expression usually involves the use of an expression vector that is able to replicate efficiently in a host cell, such that the host cell accumulates many copies of the expression vector, and, in turn, synthesises high levels of DIP 1. For the purposes of the present invention, transient expression systems are useful e.g. for identifying DIP 1 mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing DIP 1 expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing DIP 1. Suitable prokaryotes include eubacteria, such as Gram-negative or Gram-positive organisms, such as E. coli, e.g. E. coli K-12 strains, DH5a and HB101, or Bacilli. Further hosts suitable for DIP 1 encoding vectors include eukaryotic microbes such as filamentous fungi or yeast, e.g. Saccharomyces cerevisiae. Higher eukaryotic cells include insect and vertebrate cells, particularly mammalian cells. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vito culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of DIP 1 -encoding nucleic acid to form DIP 1. The precise amounts of DNA encoding DIP 1 may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby DIP 1 encoded by the DNA is expressed. The composition of suitable media is known to those in the art, so that they can be readily prepared. Suitable culturing media are also commercially available.

While the DNA provided herein may be expressed in any suitable host cell, e.g. those referred to above, preferred for expression of DNA encoding functional DIP 1 are eukaryotic expression systems such as baculovirus-based systems and, particularly, mammalian expression systems, including commercially available systems and other systems known to those of skill in the art.

In preferred embodiments, DIP 1 encoding DNA is ligated into a vector, and introduced into suitable host cells to produce transformed cell lines that express DIP 1. The resulting cell lines can then be produced in quantity for reproducible qualitative and/or quantitative analysis of the effect(s) of potential drugs affecting DIP 1 function. Thus DIP 1 expressing cells may be employed for the identification of compounds, particularly small antagonising molecules interfering with DIP 1 function are useful. An alternative to achieve an antagonistic effect is to rely on overexpression of antisense DIP 1 RNA. Thus host cells expressing DIP 1 are useful for drug screening and it is a further object of the present invention to provide a method for identifying compounds which modulate and preferable reduce the activity of DIP 1, said method comprising exposing cells containing heterologous DNA encoding DIP 1, wherein said cells produce functional DIP 1, to at least one compound or signal whose ability to modulate the activity of said DIP 1 is sought to be determined, and thereafter monitoring said cells for changes caused by said modulation. Such an assay enables the identification of agonists, antagonists and modulators of DIP 1.

Cell-based screening assays can be designed e.g. by constructing cell lines in which the expression of a reporter protein, i.e. an easily assayable protein, such as β galactosidase, chloramphenicol acetyltransferase (CAT) or luciferase, is dependent on DIP 1. Such an assay enables the detection of compounds that directly modulate DIP 1 function, e.g. compounds that induce DIP 1, or compounds that promote other cellular functions required for the activity of DIP 1.

It has been found that DIP 1 is induced in neural cells upon Deprenyl® treatment. Thus the present invention also provides a method to exogenously affect DIP 1 dependent processes occurring in such cells. DIP 1 producing cells, e.g. neural cells, can be contacted with a test compound, and the modulating effect(s) thereof can then be evaluated by comparing the DIP 1 induction response in the presence and absence of test compound, or relating the DIP 1 induction response of test cells, or control cells (i.e., cells that do not express DIP 1), to the presence of the compound. The same strategy can be used to observe the effect of test compounds which modulate the downstream effects of DIP 1.

As used herein, a compound or signal that modulates the activity of DIP 1 refers to a compound that alters the level or activity of DIP 1 in such a way that the activity of DIP 1 is different in the presence of the compound or signal (as compared to the absence of said compound or signal).

Thus, the invention provides compounds which are modulators of DIP 1 activity. Preferably, such compounds induce DIP 1 in neural cells.

Advantageously, DIP 1-inducing compounds according to the invention may be selected from the following:

(II) 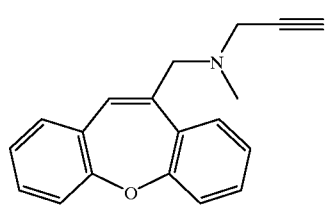
(III) 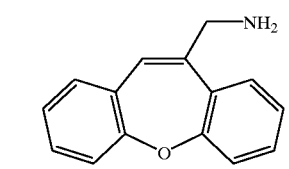
(IV) 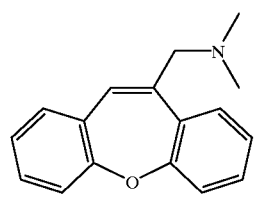
(V) 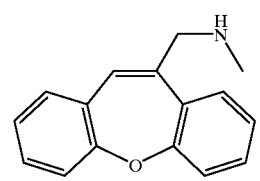
(VI) 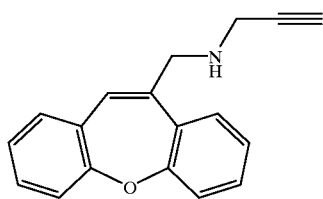
(VII) 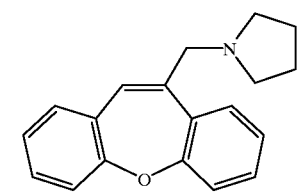
(VIII) 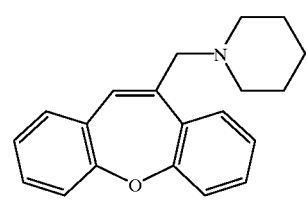
-continued
(IX) 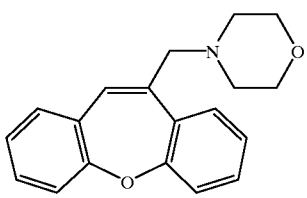
(X) 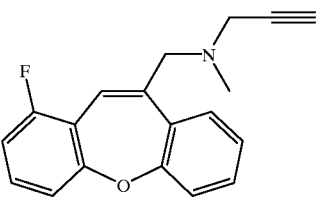
(XI) 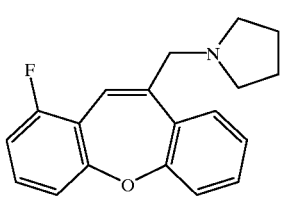
(XII) 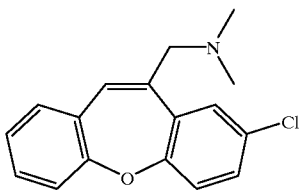
(XIII) 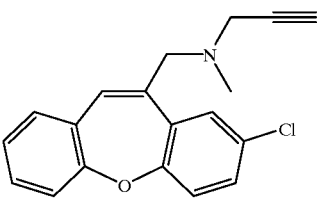
(XIV) 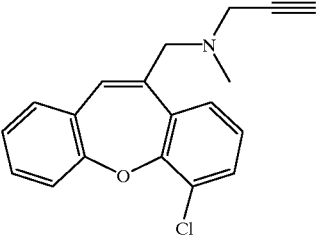
(XV) 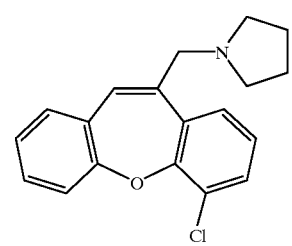

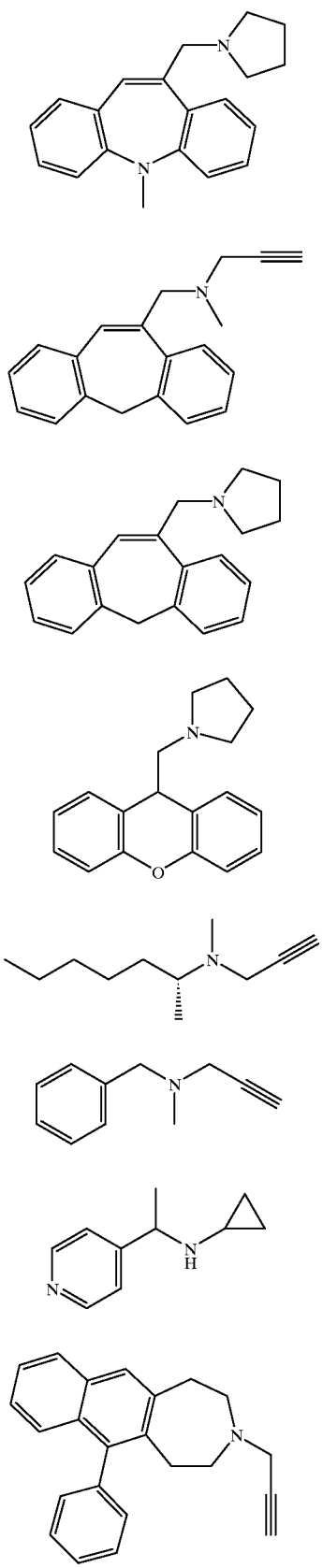

Further classes of compounds involving substitutions, side chain alterations and ring modifications may be envisaged. Such further compound may be assayed by measuring the activity thereof in the induction of DIP 1 synthesis or increasing DIP 1 activity.

The invention therefore includes a method of screening a compound for an ability to rescue neural cells from apoptosis comprises contacting a neural cell with the compound and observing the levels of DIP 1 activity, an elevated level being indicative of ability of the compound ability to rescue neural cells from apoptosis. Moreover, the invention provides a composition for rescuing neural cells from apoptosis, which composition is effective to increase the activity of DIP 1 in neural cells.

In a further aspect of the invention, there is provided a method for treating a patient suffering from a neural condition comprising administering to the patient a pharmaceutically effective amount of a composition effective to modulate the activity of DIP 1 in neural cells. As set out above, modulation of DIP 1 activity may be achieved by altering the levels of DIP 1 expression, or altering the activity of DIP 1 on its downstream target(s). Preferably, the activity of DIP 1 is increased.

The effect of the therapy set out above will be to delay the onset and/or progress of neural apoptosis associated with neural disease.

The invention also provides a transgenic non-human mammal which has been modified to modulate the expression of endogenous DIP 1. Preferably, the transgenic non-human mammal is a transgenic mouse. For example, therefore, a transgenic mouse may be designed in which DIP 1 production is greatly reduced or eliminated Alternatively, the transgenic mouse of the invention may express elevated levels of DIP 1, or may be subject to regulation of DIP 1 expression in a developmentally or tissue-specific manner, or via control by exogenous agents. Study of such an animal provides insights into the importance of DIP 1 in vivo and it allows the mesurement of in vivo effect of neuroactive drugs such as those listed above at the molecular level.

Preferably, DIP 1 is expressed in a tissue-specific manner, advantageously through the use of tissue-specific control sequences, such as promoters, enhancers or locus control elements. Particularly preferred is the TH gene promoter, which directs tissue-specifc expression in neuronal cells (Joh et al., Mol. Brain Res., 1994, 27, 281–289). Such control sequences may be used in association with DIP 1 control sequences in order to couple tissue specificity with responsiveness to anti-apoptotic drugs.

The control sequences may be operably linked to the DIP 1 coding sequence, or to that of a reporter gene, which will allow monitoring of DIP 1 control sequence induction.

Moreover, since the polypeptide according to the invention is associated with the apoptotic process in neural cells, the invention provides a composition comprising a nucleic acid encoding a polypeptide according to the invention or an antagonist thereto for use as a medicament in the treatment or diagnosis of neural disease.

In a preferred embodiment, there is provided a transcription unit encoding a polypeptide according to the invention or an antagonist thereto for use in a method of treatment of a neural or other condition, for example a condition involving aberrant DIP 1 gene expression, by gene therapy techniques. The transcription unit provided according to the present aspect of the invention comprises regulatable control regions which include a promoter, together with one or more enhancers and/or LCRs. The transcription unit may be delivered to the subject by any suitable means, including viral vectors, especially retroviral vectors, adeno- and adeno associated viral vectors, non-viral delivery systems, including liposomal and antibody targeted delivery systems, direct uptake of naked DNA and transfer of ex vivo transfected cells. The target tissue is advantageously a neural tissue.

In accordance with yet another embodiment of the present invention, there are provided antibodies specifically recognising and binding to DIP 1. For example, such antibodies may be generated against the DIP 1 having the amino acid sequences set forth in SEQ ID No. 1. Alteratively, DIP 1 or DIP 1 fragments (which may also be synthesised by in vitro methods) are fused (by recombinant expression or an in vitro peptidyl bond) to an immunogenic polypeptide and this fusion polypeptide, in turn, is used to raise antibodies against a DIP 1 epitope.

Anti-DIP 1 antibodies are recovered from the serum of immunised animals. Alternatively, monoclonal antibodies are prepared from cells in vitro or from in vivo immunised animals in conventional manner.

The antibodies of the invention are useful for studying DIP 1 tissue localisation, screening of an expression library to identify nucleic acids encoding DIP 1 or the structure of functional domains, as well as for the purification of DIP 1, and the like. Moreover, they are useful for monitoring the action of neuroactive drugs in vivo.

Antibodies according to the invention may be whole antibodies of natural classes, such as IgE and IgM antibodies, but are preferably IgG antibodies. Moreover, the invention includes antibody fragments, such as Fab, $F(ab')_2$, Fv and ScFv. Small fragments, such Fv and ScFv, possess advantageous properties for diagnostic and therapeutic applications on account of their small size and consequent superior tissue distribution.

The antibodies according to the invention may be indicated for the diagnosis of neural disease. Accordingly, they may be altered antibodies comprising an effector protein such as a label. Especially preferred are labels which allow the imaging of the distribution of the antibody in neural cells in vivo. Such labels may be radioactive labels or radioopaque labels, such as metal particles, which are readily visualisable within the body of a patient. Moreover, the may be fluorescent labels or other labels which are visualisable on tissue samples removed from patients.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification [see international patent application WO 90/07861 (Protein Design Labs)].

Antibodies according to the invention may be obtained from animal serum, or, in the case of monoclonal antibodies or fragments thereof, produced in cell culture. Recombinant DNA technology may be used to produce the antibodies according to established procedure, in bacterial or preferable in mammalian cell culture. The selected cell culture system preferably secretes the antibody product.

Therefore, the present invention includes a process for the production of an antibody according to the invention comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. fetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2 x YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balbic mice optionally pre-treated with pristane, and, after one to two weeks, ascitic fluid is taken from the animals.

The cell culture supematants are screened for the desired antibodies, preferentially by immunofluorescent staining of cells expressing DIP 1, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-)affinity chromatography, e.g. affinity chromatography with DIP 1 protein or with Protein-A.

The invention further concerns hybridoma cells secreting the monoclonal antibodies of the invention. The preferred hybridoma cells of the invention are genetically stable, secrete monoclonal antibodies of the invention of the desired specificity and can be activated from deep-frozen cultures by thawing and recloning.

The invention also concerns a process for the preparation of a hybridoma cell line secreting monoclonal antibodies directed to DIP 1, characterised in that a suitable mammal, for example a Balb/c mouse, is immunised with purified DIP 1 protein, an antigenic carrier containing purified DIP 1 or with cells bearing DIP 1, antibody-producing cells of the immunised mammal are fused with cells of a suitable myeloma cell line, the hybrid cells obtained in the fusion are cloned, and cell clones secreting the desired antibodies are selected. For example spleen cells of Balbic mice immunised with cells bearing DIP 1 are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 10 and $10^7$ and $10^8$ cells of human tumour origin which express DIP 1 containing a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

The invention also concerns recombinant DNAs comprising an insert coding for a heavy chain variable domain and/or for a light chain variable domain of antibodies directed to the extracellular domain of DIP 1 as described hereinbefore. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed DIP 1 can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the abovementioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli,* to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

The invention therefore also concerns recombinant DNAs comprising an insert coding for a heavy chain murine variable domain of an antibody directed DIP 1 fused to a human constant domain γ, for example γ1, γ2, γ3 or γ4, preferably γ1 or γ4. Likewise the invention concerns recombinant DNAs comprising an insert coding for a light chain murine variable domain of an antibody directed to DIP 1 fused to a human constant domain κ or λ, preferably κ.

In another embodiment the invention pertains to recombinant DNAs coding for a recombinant DNA wherein the heavy chain variable domain and the light chain variable domain are linked by way of a DNA insert coding for a spacer group, optionally comprising a signal sequence facilitating the processing of the antibody in the host cell and/or a DNA coding for a peptide facilitating the purification of the antibody and/or a DNA coding for a cleavage site and/or a DNA coding for a peptide spacer and/or a DNA coding for an effector molecule.

The DNA coding for an effector molecule is intended to be a DNA coding for the effector molecules useful in diagnostic applications. The DNA encoding such an effector can be prepared by methods well known in the art.

In the case of a diagnostic composition, the antibody is preferably provided together with means for detecting the antibody, which may be enzymatic, fluorescent, radioisotopic or other means. The antibody and the detection means may be provided for simultaneous, simultaneous separate or sequential use, in a diagnostic kit intended for the diagnosis of neural disease.

What is claimed is:

1. An isolated nucleic acid encoding an N,N-dimethyl-N-2-propynyi-benzeneethanamine-induced protein 1 (DIP 1) having the sequence of SEQ ID NO:1.

2. The nucleic acid according to claim 1 further comprising a functional heterologous control element.

3. The nucleic acid of claim 2 wherein the functional control element is a promoter or an enhancer.

4. The nucleic acid of claim 2 in a cell.

* * * * *